US00PP33329P2

(12) United States Plant Patent
Clark

(10) Patent No.: US PP33,329 P2
(45) Date of Patent: Aug. 10, 2021

(54) BLACKBERRY PLANT NAMED 'APF-238T'

(50) Latin Name: ***Rubus subgenus Rubus* Watson**
Varietal Denomination: APF-238T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/880,780

(22) Filed: May 21, 2020

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark et al. |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz et al. |
| PP26,405 | P3 | 2/2016 | Clark et al. |
| PP26,413 | P3 | 2/2016 | Ortiz et al. |
| PP26,990 | P3 | 8/2016 | Clark |
| PP27,032 | P2 | 8/2016 | Clark |
| PP27,401 | P3 | 11/2016 | Clark et al. |
| PP28,598 | P3 | 11/2017 | Clark |

OTHER PUBLICATIONS

Zurn et al., Validating Blackberry Seedling Pedigrees and Developing and Improved Multiplexed Microsatellite Fingerprinting Set, J. Amer. Soc. Hort. Aci. 143(5):381-390. 2018 https://doi.org/10.21273/JASHS04474-18.*
U.S. Appl. No. 16/602,884, filed Dec. 18, 2019.
U.S. Appl. No. 16/602,892, filed Dec. 19, 2019.
U.S. Appl. No. 16/873,341, filed Mar. 24, 2020.
U.S. Appl. No. 16/880,798, filed May 21, 2020.
Blaedow, K et al. Blackberry Advanced Breeding Line Trial: Bringing New Cultivars to NC. Poster presented at 2020 NARBA Conference. Mar. 3-6, 2020. St Louis, MO.
Blaedow, K. et al. Blackberry Advanced Breeding Line Trial: Bringing New Cultivars to NC. Poster presented North Caroline State Annual Extension Conference Oct. 28-Oct. 31, 2019. Raleigh, NC.
Clark, J.R. 2013. 'Osage' thornless blackberry. HortScience 48:909-912.
Clark, J.R. et al. 2008. 'Natchez' thomless blackberry. HortScience 43:1897-1899.
Clark, J.R. et al. 2005. 'Ouachita' thomless blackberry. HortScience 40:258-260.
Clark, J.R. et al. 2011. APF-45 primocane-fruiting blackberry. HortScience 46.4 (2011): 670-673.
Clark, J.R. et al. 2019. 'Caddo' thornless blackberry. Hortscience 54:1632-1636. https://doi.org/10.21273/HORTSCI14119-19.
University of Arkansas. Blackberries—Ponca. Flyer. Nov. 1, 2019.
USDA Plant Hardiness Zone Map. 2013. United States Department of Agriculture—Agricultural Research Service. May 17, 2013. http://planthardiness.ars.usda.gov/PHZMWeb/.

* cited by examiner

*Primary Examiner* — Anne Marie Grunberg
(74) *Attorney, Agent, or Firm* — Quarles & Brady LLP

(57) ABSTRACT

Description and specifications of a new and distinct cultivar of blackberry plant named 'APF-238T' which originated from seed produced by a hand-pollinated cross of 'APF-27' (non-patented, unreleased genotype) x 'APF-77' (U.S. Plant Pat. No. 24,249). This new cultivar of blackberry plant can be distinguished by its medium-sized berries with sweet flavor, produced on very healthy plants with erect, thornless canes that are primocane-fruiting.

4 Drawing Sheets

Latin name: *Rubus* subgenus *Rubus* Watson.
Varietal denomination: 'APF-238T'.

BACKGROUND

The new primocane-fruiting cultivar of blackberry called 'APF-238T' is described herein. The new cultivar originated from a hand-pollinated cross of 'APF-27' (non-patented, unreleased genotype) x 'APF-77' (U.S. Plant Pat. No.

24,249) made in 2006. The seeds resulting from this controlled hybridization were germinated in a greenhouse in the spring of 2007 and planted in a field near Clarksville, Ark. (West-Central Arkansas). The seedlings fruited in the summer of 2009 and one seedling, designated 'APF-238T,' and was selected for its medium-sized berries with sweet flavor, produced on very healthy plants with erect, thornless canes that are primocane-fruiting.

SUMMARY OF THE INVENTION

The new and distinct cultivar of blackberry originated from a hand-pollinated cross of 'APF-27' (non-patented, unreleased genotype) x 'APF-77' (U.S. Plant Pat. No. 24,249) made in 2006. The botanical designation of the new cultivar of blackberry is *Rubus* L. subgenus *Rubus* Watson. The seeds resulting from this controlled hybridization were germinated in a greenhouse in the winter to early spring of 2007 and planted in a field near Clarksville, Ark. The seedlings fruited in the summer of 2009 on floricanes and one seedling, designated 'APF-238T,' and was selected for its medium-sized berries with sweet flavor, produced on very healthy plants with erect, thornless canes that are primocane-fruiting.

During 2009, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2009 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants from which the images were taken were 3 years old.

DETAILED DESCRIPTION OF THE NEW CULTIVAR 'APF-238T'

Figure 1:
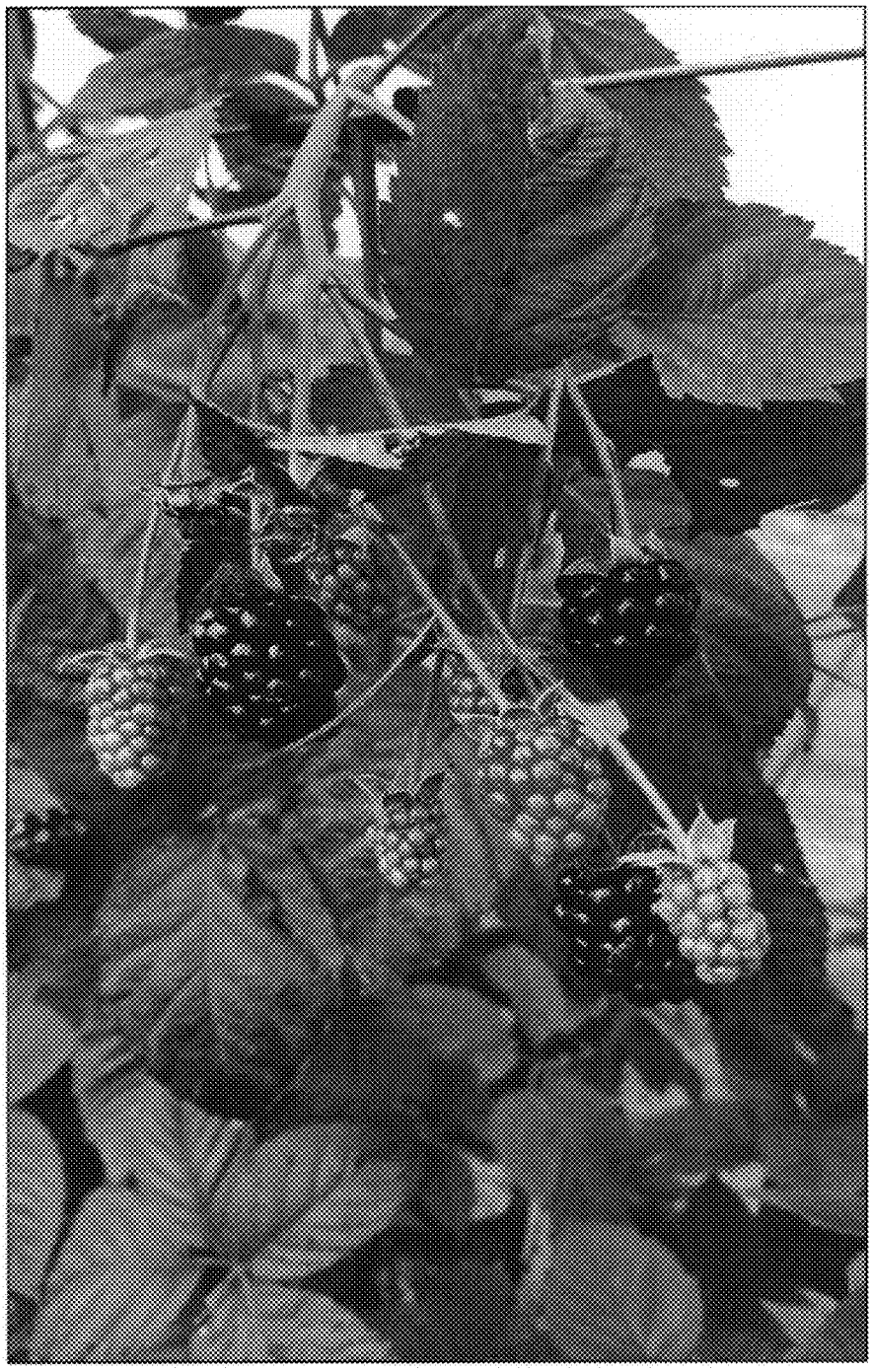
FIG. 1 is a photograph of blackberry canes of 'APF-238T' with ripe fruit on the plant.
Figure 2:
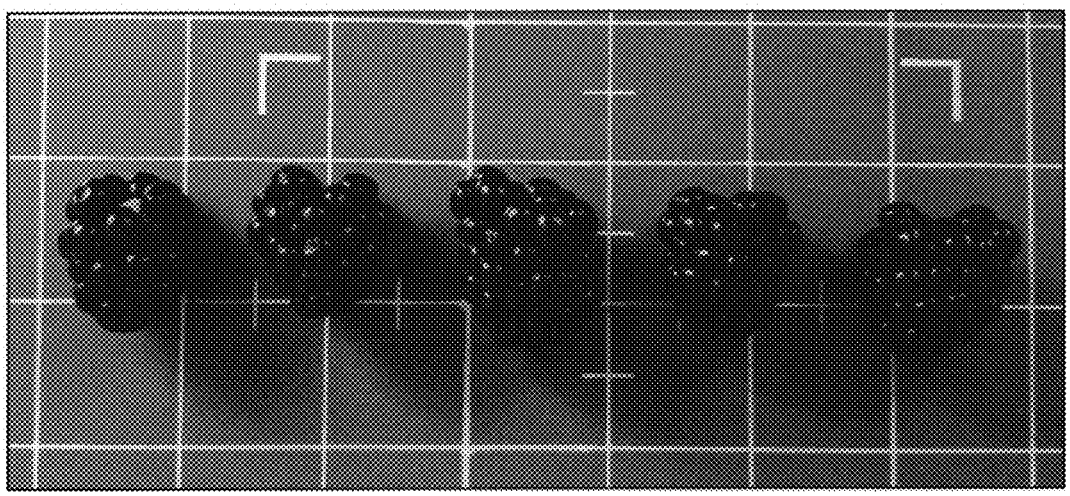
FIG. 2 is a photograph of ripe fruit of 'APF-238T'.
Figure 3:
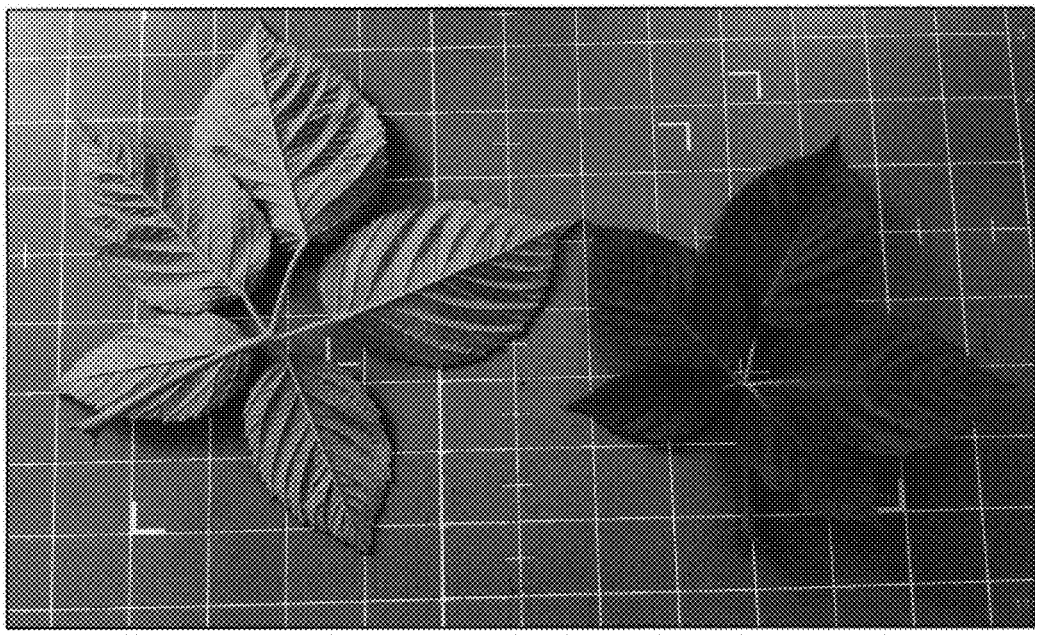
FIG. 3 is a photograph showing the abaxial and adaxial sides of a primocane leaf of 'APF-238T'.
Figure 4:
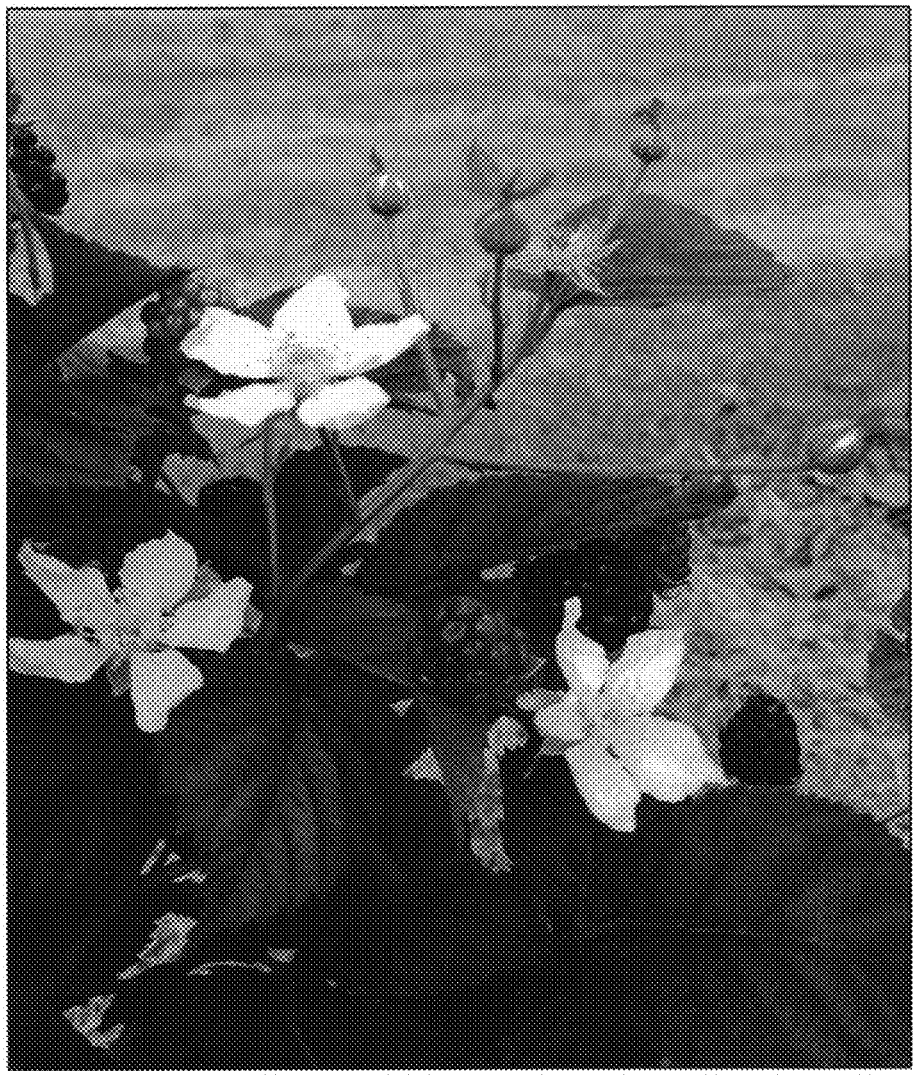
FIG. 4 is a photograph showing primocane fruit and flowers of 'APF-238T'.

Plants and fruit of this new cultivar differ phenotypically from its parents. The new cultivar has thornless canes, is earlier in primocane bloom, and has more intense primocane bloom expression compared to its female parent 'APF-27.' The new cultivar has thornless canes, is earlier ripening, has smaller but firmer fruit than its male parent 'APF-77.' Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are resistant to anthracnose [*Elsinoe veneta* (Burkh.) Jenkins], and plants have shown no evidence of susceptibility to orange rust [*Gymnoconia nitens* (Schwein.) F. Kern and H. W. Thurston.]. The plants have low susceptibility to cane and leaf rust (*Kuehneola uredines* (Link) Arthur). No screening has been done for resistance to double blossom/rosette [*Cercosporella rubi* (Wint.) Plakidas]

The floricane bloom period of the new cultivar begins on average 14 April for 10% bloom and 21 April for 50% bloom and was very near that of 'APF-45' (U.S. Plant Pat. No. 22,449). Primocane bloom begins 8 June and is 21 days before 'APF-45'.

Floricane fruit of the new cultivar has an average first harvest date of 4 June and is near or 2-3 days earlier than that of 'APF-45', while primocane fruit average first harvest date was 10 July and was 21 days earlier than 'APF 45.' The average floricane fruiting period is 30 days while the primocane harvest date can extend to more than 40 days depending on environmental conditions.

Fruit yields of the new cultivar on floricanes are on average 2.1 kg (4.7 lb/plant), lower than that of 'APF-45' in West-Central Arkansas.

The fruit is round and glossy with a uniform black finish. The floricane and primocane fruit is medium (ave. 6.0 g and 6.5 g, respectively) and usually 1.0 g or more smaller than 'APF-45'. Fruit size can decline near the end of the floricane harvest season, but is usually maintained for the entire primocane season. The new cultivar exhibits excellent floricane fruit fertility with full drupelet set and if bloom and fruit development temperatures remain below 90° F. (32° C.) the primocane fruit set is excellent; higher temperatures can lead to reduced set and reduced berry size. Fruit firmness is not as high as 'APF-45'. Storage potential of fresh fruit of the new cultivar is not as high as 'APF-45' as it has higher leakage as well as softer berries after storage. The dry seed weight for the new cultivar averaged 3.0 mg/seed (floricane fruit), smaller than 'APF-45'.

The fresh fruit rates very well in flavor and is a noteworthy attribute of the cultivar and is comparable to or exceeding that of 'APF-45'. Consistent excellent flavor was noted at repeated observations of fruit of this cultivar over the years of evaluation including after rain events that can reduce flavor and overall fruit quality. The flavor is sweet and low acid, with desirable aromatics. The soluble solids concentration averages 13.2% (floricane) and 12.8% (primocanes) on shiny black fruit, comparable to higher than 'APF 45'. Fruit and flower clusters are medium-large, cymose, and are mostly borne on the periphery of the plant canopy, providing easy access to harvest.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were two years old, unless otherwise noted, and grown on a fine sandy loam soil with trickle irrigation at or near Clarksville, Ark. The plants were fertilized near budbreak with complete or nitrogen fertilizer and had an additional nitrogen fertilizer application in early July. Primocanes were tipped at approximately 1.14 m (45 inches) and grown in a hedgerow training system. Weeds were controlled with pre- and post-emergent herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Medium. Plants are grown in a hedgerow and primocanes tipped at approx., 1.14 m; plants in this system range in size from approx. 107-140 cm tall and 91-102 cm wide.

*Growth habit*.—Upright, moderate vigor, canes erect; suckers from the crown.

*Growth rate*.—Floricane first budbreak 8 February; first emergence of primocanes is 28 March and primocanes reach tipping height (107 cm) on 10 April.

Productivity:

*Floricane*.—2.1 kg (4.7 lb/plant).

*Cold hardiness*.—Hardy to 1.4° F. (−17° C.) or lower. The low temperature of 1.4° F. was the lowest the cultivar has been exposed to and fruited successfully after this exposure.

Canes:

*Floricane* (*winter or dormant cane*).—Cane diameter: base 1.25 cm; midpoint 0.91 cm; terminal 0.79 cm. Cross-section of dormant cane: angular. Internode length: base 5.99 cm; midpoint 5.96 cm; terminal 5.68 cm. Floricane color: base Greyed Purple (183A); midpoint Greyed Purple (183A); terminus Greyed Purple (183A).

*Primocane* (*current-season cane; late summer*).—First date of emergence: 28-March. Average number of new canes per year: 4-5. Cane diameter: base 1.45 cm; midpoint 1.14 cm; terminal 0.49 cm. Internode length: base 5.88 cm; midpoint 6.14 cm; terminal 2.27 cm. Primocane color: base Yellow Green Group (145A); midpoint Yellow Green Group (145A); terminus Yellow Green Group (145A). The shaded portion of canes are overall Yellow Green Group (149A). Anthocyanin coloration mildly present on floricanes and primocanes with color most prevalent on sun-exposed canes. Thorn density (per 30 cm of cane length): this plant is thornless. Glandular hairs on young shoot: Absent or few. Disease resistance: Moderate resistance to anthracnose, and plants appear resistant to orange rust. Low susceptibility to cane and leaf rust. No screening has been done for resistance to double blossom/rosette. Lateral branching after tipping (measured at the end of growing season): Average number of lateral branches: 7.5; distribution full length of cane.

Foliage:

*Primocane*.—Leaves: large; mature compound leaf width 20.1 cm; length 17.6 cm; overall shape: palmate. Glossiness: Abaxial: dull, pubescence lightly present; adaxial: moderate gloss, pubescence lightly present. Leaflet: Width 6.13 cm; length 8.72 cm; shape ovate with acute apex and rounded base; margin is serrated: serration teeth length 0.33 cm and width 0.34 cm; number of leaflets per compound leaf 5; venation pinnate; young leaf abaxial vein color Yellow Green Group (144B); young leaf adaxial vein color Yellow Green Group (145A); mature leaf abaxial leaf vein color Yellow Green Group (145C); material leaf adaxial vein color Yellow Green Group (145A); no lobing on terminal leaflets; terminal leaflet shape in cross-section is V-shaped; undulation of the terminal leaflet margin is absent; terminal leaflet blistering between veins is absent to weak. Leaf Color: Base abaxial Green Group (137B); adaxial Green Group (137B); midpoint abaxial Green Group (137B); adaxial Green Group (141A); terminal abaxial Green Group (141A); adaxial Green Group (141A). Petioles: Length: 3.03 cm; color: abaxial Yellow Green Group (146A) and adaxial Greyed Purple Group (183D); diameter 0.2 cm; light pubescence is present uniformly. Petiolules: Length: 5.74 cm; diameter 0.31 cm; color: abaxial Yellow Green Group (146B), adaxial Greyed Purple Group (183D); light pubescence is present uniformly. Stipules: 2 per leaf; Length: 1.31 cm; width: 0.10 cm; texture pubescence is light on abaxial surface and absent on adaxial surface. Shape: overall shape subulate; apex acuminate; base rounded; margin entire (smooth); color: abaxial Greyed Purple Group (184B), adaxial Greyed Purple Group (184A).

*Floricane*.—Leaves: Medium; mature compound leaf width 14.79 cm; length 14.16 cm; overall shape: palmate. Average date of leaf bud burst: 8 February. Glossiness: Abaxial: dull, pubescence lightly present; adaxial: no gloss, pubescence not present. Leaflet: Width 5.26 cm; length 7.51 cm; shape cordate with acute apex and oblique base; margin serrated, with serration teeth length 0.26 cm and width at base 0.33 cm; number of leaflets per compound leaf 3; venation pinnate; young leaf abaxial vein color Yellow Green Group (144B); young leaf adaxial vein color Yellow Green Group (144D); mature leaf abaxial leaf vein color (145B); mature leaf adaxial vein color Yellow Green Group 144A; no lobing on terminal leaflets; terminal leaflet shape in cross-section is V-shaped; undulation of the terminal leaflet margin is absent; terminal leaflet blistering between veins is absent to weak. Leaf Color: base abaxial Yellow Green Group (147B); adaxial Green Group (139A); midpoint abaxial Yellow Green Group (147B); adaxial Green Group (139A); terminal abaxial Yellow Green Group (147B); adaxial Green Group (139A). Petioles: Length 3.96 cm; diameter 0.23 cm; color: abaxial Yellow Green Group (145A); adaxial Yellow Green Group (144A); texture pubescence is light on abaxial and adaxial surfaces. Petiolules: Length 2.11 cm; diameter 0.16 cm; Color: abaxial side is Yellow Green Group (145A); adaxial side is Yellow Green Group (144A); texture is uniformly light pubescence. Stipules: 2 per leaf; length 1.06 cm; width: 0.08 cm; texture pubescence is light on abaxial side and absent on adaxial side. Shape: overall shape subulate; apex acuminate; base rounded; margin: entire (smooth); color: abaxial side is Yellow Green Group (147C); adaxial side is Yellow Green Group (148A).

Flowers:

*Floricane*.—Date of bloom: First bloom 14 April; 50% bloom 21 April. Reproductive organs: Stamens — erect, numerous. Pistils — numerous. Pollen — normal, fertile, and abundant. Flowers: Diameter: 4.99 cm; depth: 2.23 cm; shape: overall: rotate; symmetry: actinomorphic. Petals: Number per flower: 5; length 2.61 cm; width 1.91 cm; shape: overall: obovate; apex: obtuse; margin: entire (smooth); base: rounded; color: White Group (155D); identical color on both abaxial and adaxial surface of petals; texture: abaxial: smooth, no pubescence; adaxial: smooth, no pubescence. Average number flowers per cluster: 5. Sepals: Number per flower: 5; length 1.02; width: 0.56 cm; shape: overall: deltoid; apex: acuminate; margin: entire (smooth); base: truncate: texture: abaxial: heavy pubescence; adaxial: moderate pubescence; color: Abaxial: Green Group (138B); adaxial: Green Group (138A). Pedicel: Length: 3.75 cm; Color: Yellow Green group (144A); texture: heavy pubescence. Peduncle: Length: 0.50 cm; width: 0.42 cm; color: Greyed Orange Group (166A). Cyme: type: Simple cyme; length: 12.38 cm.

*Primocane*.—Date of bloom: First bloom 8 June. Reproductive organs: Stamens — erect, numerous. Pistils — numerous. Pollen — normal, fertile, and abundant. Flowers: Diameter: 5.65 cm; depth: 1.55 cm; shape: Overall: rotate; symmetry: actinomorphic. Petals: Number per flower: 5; length 2.65 cm; width 1.77 cm; shape: overall: obovate; apex: obtuse; margin: entire (smooth); base: cuneate; color: White Group (155A); identical color on both sides of petals; texture: abaxial: smooth, no pubescence; adaxial: smooth, no pubescence. Average number flowers per cluster: 7. Sepals: Number per flower: 5; length: 2.0 cm; width: 0.65 cm; shape: overall: lanceolate; apex: aristate; margin: entire (smooth); base: truncate; texture: Both the abaxial and adaxial surface are uniformly smooth, lacking pubescence; color: abaxial: Yellow Green Group (146C); adaxial: Yellow Green Group (145A). Pedicel: Length: 3.41 cm; Color: Green Group (143A); texture: heavy pubescence. Peduncle: Length: 0.32 cm; width: 0.27 cm; color: Yellow-Green Group (147A). Cyme: Type: simple; length: 13.32 cm.

Fruit:

*Floricane*.—Maturity — Average first ripe date 4 June; average fruiting period 30 days. Size: Medium, average 6.0 g. Diameter of fruit at primary position on inflorescence: equator 2.01 cm; base pole 1.94 cm; terminal pole 1.76 cm. Diameter of fruit at secondary positions on inflorescence: equator 1.95 cm; base pole 1.79 cm; terminal pole 1.68 cm. Primary Fruit: Length: 2.41 cm; shape: round; color: Black Group (202A). Drupelet size: 0.53 cm. Drupelet number per fruit: 31.8. Seed: Average length 0.23 cm; width 0.20 cm; wet weight 4.06 mg; dry weight 3.04 mg; color wet: Greyed Purple Group (184A); color dry: Red Purple Group (73D). Soluble solids: 13.2%. pH: 3.14. Acidity: 1.16 g/L expressed as citric acid. Processed quality: Not evaluated for processing. Uses: Commercial use for local-market production and home garden production.

Fruit:

*Primocane*.—Maturity — Average first ripe date 10 July; average fruiting period 40 days and can extend longer. Size: Medium, average 6.5 g. Diameter of fruit at primary position on inflorescence: equator 2.10 cm; base pole 2.02 cm; terminal pole 1.76 cm. Diameter of fruit at secondary positions on inflorescence: equator 2.08 cm; base pole 2.04 cm; terminal pole 1.43 cm. Primary Fruit: Length: 2.61 cm; shape: round: color: Black Group (202A). Drupelet size: 0.60 cm. Drupelet number per fruit: 49.8. Seed: average length 0.36 cm; width 0.21 cm; wet weight: 5.84 mg; dry weight: 4.24 mg; color wet: Greyed Purple Group (183B); color dry Greyed Purple Group (183D). Soluble solids: 12.8%. pH: 3.18. Acidity: 1.13 g/L expressed as citric acid. Processed quality: Not evaluated for processing. Uses: Commercial use for local-market production and home garden production.

The cultivar: The most distinctive features of the cultivar are medium-sized berries with sweet flavor, produced on very healthy plants with erect, thornless canes that are primocane-fruiting.

I claim:

1. A new and distinct cultivar of blackberry plant named 'APF-238T,' substantially as illustrated and described herein.

* * * * *